United States Patent [19]

Magda et al.

[11] Patent Number: 5,595,726
[45] Date of Patent: Jan. 21, 1997

[54] CHROMOPHORE PROBE FOR DETECTION OF NUCLEIC ACID

[75] Inventors: Darren Magda, Cupertino, Calif.; Jonathan L. Sessler; Brent Iverson, both of Austin, Tex.

[73] Assignees: Pharmacyclics, Inc., Sunnyvale, Calif.; Board of Trustees, Univ. of TX Sys., Austin, Tex.

[21] Appl. No.: 486,311

[22] Filed: Jun. 7, 1995

Related U.S. Application Data

[63] Continuation-in-part of Ser. No. 310,501, Sep. 21, 1994, which is a continuation-in-part of Ser. No. 112,872, Aug. 25, 1993, Pat. No. 5,451,576, and a continuation-in-part of PCT/US94/06284, Jun. 9, 1994, said Ser. No. 112,872, and a continuation-in-part of Ser. No. 227,370, Apr. 14, 1994, which is a continuation-in-part of Ser. No. 75,123, Jun. 9, 1993, abandoned, which is a continuation-in-part of Ser. No. 822,964, Jan. 21, 1992, Pat. No. 5,252,720, said PCT/US94/06284, said Ser. No. 112,872, is a division of Ser. No. 822,964.

[51] Int. Cl.[6] .................................................. C07D 487/22
[52] U.S. Cl. .......................... 424/9.61; 424/1.73; 424/9.6; 435/6; 436/98; 436/177; 436/800; 436/905; 540/145; 540/465; 540/472
[58] Field of Search .................................. 540/145, 465, 540/472; 424/1.73, 9.6, 9.61; 436/98, 172, 800, 905; 435/6

[56] References Cited

U.S. PATENT DOCUMENTS

| | | | |
|---|---|---|---|
| 4,318,825 | 3/1982 | Frame | 252/428 |
| 4,647,447 | 3/1987 | Gries et al. | 524/9 |
| 4,835,263 | 5/1989 | Nguyen et al. | 536/27 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,141,911 | 8/1992 | Meunier et al. | 502/159 |
| 5,162,509 | 11/1992 | Sessler et al. | 534/15 |
| 5,242,797 | 9/1993 | Hirschfeld | 435/7 |
| 5,252,720 | 10/1993 | Sessler et al. | 534/11 |
| 5,256,399 | 10/1993 | Sessler et al. | 424/9 |
| 5,272,056 | 12/1993 | Burrows et al. | 435/6 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,369,101 | 11/1994 | Sessler et al. | 534/13 |
| 5,371,199 | 12/1994 | Therien et al. | 534/11 |
| 5,432,171 | 7/1995 | Sessler et al. | 514/185 |
| 5,439,570 | 8/1995 | Sessler et al. | 254/157.17 |
| 5,451,576 | 9/1995 | Sessler et al. | 514/185 |
| 5,457,183 | 10/1995 | Sessler et al. | 534/11 |

FOREIGN PATENT DOCUMENTS

| | | |
|---|---|---|
| 0111418 | 6/1984 | European Pat. Off. . |
| 0196515 | 10/1986 | European Pat. Off. . |
| 0214908 | 3/1987 | European Pat. Off. . |
| 0233701A2 | 8/1987 | European Pat. Off. . |
| 2697254 | 4/1994 | France . |
| WO90/02747 | 3/1990 | WIPO . |
| 90/01208 | 8/1990 | WIPO . |
| WO90/10633 | 9/1990 | WIPO . |
| 91/19730 | 12/1991 | WIPO . |
| 92/01781 | 2/1992 | WIPO . |
| WO93/14093 | 7/1993 | WIPO . |
| WO94/09003 | 4/1994 | WIPO . |
| WO94/29316 | 12/1994 | WIPO . |
| WO95/21845 | 8/1995 | WIPO . |

OTHER PUBLICATIONS

Casas et al., "Preparation of Hybrid DNA Cleaver-Oligonucleotide Molecules Based on a Metallotris(methylpyridiniumyl)porphyrin Motif", *Bioconjugate Chem.*, 4:366–371 (1993).

Abid et al., "Lanthanide Complexes of Some Macrocyclic Schiff Bases Derived from Pyridine-2,6-dicarboxaldehyde and δω-Primary Diamines", *Inorg. Chim. Acta*, 95:119–125, 1984.

Acholla et al., "Binucleating Tetrapyrrole Macrocycles", *J. Am. Chem. Soc.*, 107:6902–6908, 1985.

Acholla et al., "A Binucleating Accordian Tetrapyrrole Macrocycle", *Tetrahedron Lett.*, 25:3269–3270, 1984.

Ansell, "X–Ray Crystal Structure of the Pentagonal Bipyramidal Nickel(11) Complex [Ni$^{11}$(L)(H$_2$O)$_2$](BF$_4$)$_2$ and the Selective Stabilisation of the Nickel(1) Oxidation State by a Quinquedentate Macrocyclic Ligand", *J. Chem. Soc., Chem. Commun.* pp. 546–547, 1982.

Bauer et al., "Sapphyrins: Novel Aromatic Pentapyrrolic Macrocycles", *J. Am. Chem. Soc.*, 105:6429–6436, 1983.

Broadhurst et al., "Preparation of Some Sulphur–containing Polypyrrolic Macrocycles. Sulphur Extrusion from a meso-Thiaphlorin", *J. Chem. Soc., Chem. Commun.* pp. 807–809, 1970.

Broadhurst et al., "18– and 22–π–Electron Macrocycles Containing Furan, Pyrrole, and Thiophen Rings", *J. Chem. Soc., Chem. Commun.* pp. 1480–1482, 1969.

(List continued on next page.)

Primary Examiner—Richard L. Raymond
Attorney, Agent, or Firm—Jacqueline S. Larson

[57] ABSTRACT

The present invention is directed to chromophoric probes for use in detecting nucleic acid sequences. More particularly, the invention is directed to probes that comprise a texaphyrin chromophore molecule covalently coupled or conjugated to a site-directing molecule, the site-directing molecule having affinity for a biological receptor or a nucleic acid sequence. In one embodiment of the invention, the probe comprises a texaphyrin chromophore conjugated to an oligonucleotide having complementary binding affinity for a target nucleic acid sequence.

20 Claims, 2 Drawing Sheets

OTHER PUBLICATIONS

Broadhurst et al., "New Macrocyclic Aromatic Systems Related to Porphins", *J. Chem. Soc., Chem. Commun.* pp. 23–24, 1969.

Broadhurst et al., "The Synthesis of 22 π–Electron macrocycles. Sapphyrins and Related Compounds", *J. Chem. Soc. Perkin Trans.*, 1;2111–2116, 1972.

Cuellar et al., "Synthesis and Characterization of Metallo and Metal–Free Octaalkylphthalocyanines and Uranyl Decaalkysuperphthalocyanines", *Inorg. Chem.*, 20:3766–3770, 1981.

Day et al., "Large Metal Ion–Centered Template Reactions. A Uranyl Complex of Cyclopentakis (2–iminoisoindoline)", *J. Am. Chem. Soc.*, 97:4519–4527, 1975.

De Cola et al., "Hexaaza Macrocyclic Complexes of the Lanthanides", *Inorg. Chem.*, 25:1729–1732, 1986.

Dougherty, "Photosensitizers: Therapy and Detection of Malignant Tumors", *Photochem. Photobiol.*, 45:879–889, (1987).

Gosmann et al., "Synthesis of a Fourfold Enlarged Porphyrin with an Extremely Large, Diamagnetic Ring–Current Effect", *Angew. Chem., Int. Ed Engl.*, 25:1100–1101, (1986).

Gossauer, "Syntheses of Some Unusual Polypyrrole Macrocycles", *Bull. Soc. Chim. Belg.*, 92:793–795, (1983).

Knubel et al., "Biomimetic Synthesis of an Octavinylogous Porphyrin with an Aromatic [34] Annulene System", *Angew. Chem., Int. Ed. Engl.*, 27:1170–1172, 1988.

Lauffer, "Paramagnetic Metal Complexes as Water Proton Relaxation Agents for NMR Imaging: Theory and Design", *Chem. Rev.*, 87:901–927, 1987.

LeGoff et al., "Synthesis of a [1,5,1,5] Platyrin, a 26 π–Electron Tetrapyrrolic Annulene", *J. Org. Chem.*, 52:710–711, 1987.

Marks et al., "Large Metal Ion–Centered Template Reactions. Chemical and Spectral Studies of the Superphthalocyanine Dioxocyclopentakis (1–iminoisoindolinato) uranium (VI) and Its Derivatives", *J. Am. Chem. Soc.*, 100:1695–1705, 1978.

Rexhausen et al., "The Synthesis of a New 22 π–Electron macrocycle: Pentaphyrin", *J. chem. Soc., Chem. Commun.*, p. 275, 1983.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate Porphyrin–Like Ligands", *Comm. Inorg. Chem.*, 7:333–350, 1988.

Sessler et al., "An Expanded Porphyrin: the Synthesis and Structure of a New Aromatic Pentadentate Ligand", *J. Am. Chem. Soc.*, 110:5586–5588, 1988.

Tweedle et al., "Principles of Contrast–Enhanced MRI", in Magnetic Resonance Imaging, 2nd ed. Partain, et al, Eds., W. B. Saunders: Philadelphia, vol. I (1988) 793–809.

Vogel et al., "Porphycene—a Novel Porphin Isomer", *Angew. Chem., Int. Ed. Engl.*, 25:257–259, 1986.

Vogel et al., "2,7,12,17–Tetrapropylporphycene— Counterpart of Octaethyiporphyrin in the Porphycene Series", *Angew. Chem., Int. Ed. Engl.*, 26:928–931, 1987.

Sessler et al., "A Water–Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin: Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989. Submitted as A32 in 1449 for UTSB:458.

Sessler et al., "Expanded Porphyrins: The synthesis and Metal Binding Properties of Novel Tripyrran–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived (Texaphyrin––type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "'Texaphyrin': A Novel 22 π–Electron Aromatic Pentadentate Macrocyclic Ligand", *ACS Meeting*, Los Angeles, Sep. 1988.

Sessler and Burrell, "Expanded Porphyrins," *Topics in Current Chemistry*, 161:180–273, 1991.

Sessler et al., "Synthesis and Structural Characterization of Lanthanide (III) Texaphyrins," *Inorganic Chemistry*, 32(14):3175–3187, 1993.

"2–Äthylamino–2–methyl–propanol–(1)", *Beilstein's Handbuch*, 4:785, 1950.

"Tentative Rules for Carbohydrate Nomenclature Part 1 (1969)," *Handbook of Biochemistry and Molecular Biology*, 3rd ed., Fasman, Ed., CRC Press, Cleveland, Ohio pp. 100–102.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC.

Sessler et al., "Synthesis and Applications of Schiff–Base derived Expanded Porphyrins,"*Abstracts of Papers*, Part 1, 204th ACS National Meeting, Aug. 23–28, 1992, Washington, DC.

Sessler, Jonathan L., "Texas–Sized Molecule," *Discovery*, 13(1):44–49, 1993.

Sessler et al., "Photodynamic Inactivation of Enveloped Viruses Using Sapphyrin, α 22 π–Electron Expanded Porphyrin: Possible Approaches to Prophylactic Blood Purification Protocols," *SPIE Photodynamic Therapy: Mechanisms II.* 1203:233–245, 1990.

Maiya et al., "Ground– and Excited–State Spectral and Redox Properties of Cadmium(II) Texaphyrin," *Journal of physical Chemistry*, 93(24):8111–8115, 1989.

Sessler et al., "Texaphyrins: Synthesis and Applications," *Accounts of Chemical Research*, 27(2):43–50, 1994.

Leff, "Texas 'Son–of–Porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Imaging," *Investigative Radiology*, 29(3):330–338, 1994.

Dietrich et al., "Proton Coupled Membrane Transport of Anions Mediated by Cryptate Carriers," *J. Chem. Soc. Chem. Comm.*, 1988, 11:691–692.

Dixon et al., "Molecular Recognition: Bis–Acylguanidiniums Provide a Simple Family of Receptors for Phosphodiesters," *J. Am. Chem. Soc.*, 1992, 114:365–366.

Furuta et al., "Enhanced Transport of Nucleosides and Nucleoside Analogues with Complementary Base–Pairing Agents," *Journal of the American Chemical Society*, 1991, 113:4706–4707.

Galán et al., "A Synthetic Receptor for Dinucleotides," *J. Am. Chem. Soc.*, 1991, 113:9424–9425.

Galán et al., "Selective Complexation of Adenosine Monophosphate Nucleotides By Rigid Bicyclic Guanidinium Abiotic Receptors," *Tetrahedron Letters*, 32(15):1827–1830, 1991.

Hisatome et al., "Porphyrins Coupled with Nucleoside Bases. Synthesis and Characterization of Adenine– and Thymine–Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing an Anion Binding Site, an Intercalcator Group, and a Catalytic Site," *J. Chem. Soc. Chem. Commun.*, 1988, 9:596–598.

Kimura et al., "A Study of New Bis(macrocyclic polyamine) Ligands as Inorganic and Organic Anion Receptors," *J. Org. Chem.*, 1990, 55(1):46–48.

Kimura, "Macrocyclic Polyamines as Biological Cation and Anion Complexones—An Application to Calculi Dissolution," 113–141, Topics in Current Chemistry, 128 (1985).

Li and Diederich, "Carriers for Liquid Membrane Transport of Nucleotide 5'–Triphosphates,"*J. Org. Chem.*, 1992, 47:3449–3454.

Marks and Stojakowvic, "Large Metal Ion–Centered Template Reactions. Chemical and Spectral Studies of the Superphthalocyanine Dioxocyclopentakis (1–iminoisoindolinato)uranium(VI) and Its Derivatives," *J. Am. Chem. Soc.*, 1978, 1695–1705.

Schmidtchen, "A Non–Macrocyclic Host for Binding Organic Phosphates in Protic Solvents," *Tetrahedron Letters*, 1989, 30(34):4493–4496.

Seel and Vogtle, "Molecular Recognition and Transport of Nucleobases—Superiority of Macrobicyclid Host Molecules," *Angew. Chem. Int. Ed. Engl.*, 1991, 30(4):442–444.

Sessler et al., "Anion Binding: A New Direction in Porphyrin–Related Research," *Pure & Applied Chem.*, 65(3):393–398, 1993.

Sessler et al., "Cytosine Amine Derivatives," *J. Org. Chem.*, 1992, 47:826–834.

Aoyama et al., "Multi–Point Interaction of Phosphates with Protonated Pyridylporphyrin. Discrimination of Monoalkyl and Dialkyl Phosphates," *Chemistry Letters*, 1241–1244 (1991).

Claude et al., "Binding of Nucleosides, Nucleotides and Anionic Planar Substrates by Bis–Intercaland Receptor Molecules," *J. Chem. Soc. Chem. Commun.*, 1991, 17:1182–1185.

Cramer et al., "Synthesis and Structure of the Chloride and Nitrate Inclusion Complexes of [16–Pyrimidinium crown–4]," *J. Am. Chem. Soc.*, 1991, 113:7033–7034.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine Nucleotides Using a Cytosine–Pendant Triamine Host as the Sensory Element," *Analytical Chemistry*, 1992, 64(8):960–964.

Nam–Chiang Wang et al., "Pyrrole chemistry. XVII. Alkylation of the pyrrolyl ambident anion," *Can. J. Chem.*, 55:4112–4116, 1977.

T. D. Mody et al., "Lutetium (III) Texaphyrin: A Novel Photodynamic Therapy Agent," Abstract, 22nd Annual American Society for Photobiology, Scottsdale, AZ, Jun. 25–29, 1994.

Sessler et al., "Gadolinium (III) Texaphyrin: A Novel MRI Contrast Agent," *Journal of the American Chemical Society*, 115(22):10,368–10,369, 1993.

Iverson et al., "Interactions Between Expanded Porphyrins and Nucleic Acids," *Pure Applied Chemistry*, 66(4):845–850, 1994.

Matthews et al., "Inactivation of Viruses with Photoactive Compounds," *Blood Cells*, 18(1):75–89, 1992.

Ehrenberg et al., "Spectroscopy, Photokinetics and Cellular Effect of Far–Red and Near Infrared Absorbing Photosensitizers," *Proc. SPIE–Int. Soc. Opt. Eng* 1992, 1645 (*Proc. Opt. Methods Tumor Treat. Dect.: Mech. Tech. Photodyn. Ther..*, 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al, "PDT of Tumor–Bearing Mice Using Liposome Delivered Texaphyrins," International Conference, Milan, Italy, Biosis citation only, Jun. 24–27, 1992.

Goodchild, John, "Conjugates of Oligonucleotides and Modified Oligonucleotides: A Review of Their Synthesis and Properties," *Bioconjugate Chemistry*, 1(3):165–187, 1990.

Kobayashi et al., "Uptake of Chlorophyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993.

Lin et al., "Use of EDTA Derivatization to Characterize Interactions between Oligodeoxyribonucleoside Methylphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Dreyer and Dervan, "Sequence–specific Cleavage of Single–Stranded DNA: Oligodeoxynucleotide–EDTA.Fe(II)," *Proc. Natl. Acad. Sci. USA*, 82:968–972, 1985.

Doan et al., "Sequence–targeted Chemical Modifications of Nucleic Acids by ComplimentaryOligonucleotides Covalently Linked to Porphyrins," *Nucleic Acids Research*, 15(21):8643–8659, 1987.

Doan et al., "Targeted Cleavage of Polynucleotides by Complementary Oligonucleotides Convalently Linked to Iron–Prophyrins," *Biochemistry,* 26:6736–6739, 1986.

Dervan, Peter B., "Design of Sequence–Specific DNA–Binding Melecules," *Science,* 232:464–471, 1986.

Groves and Farrell, "DNA Cleavage by a Metal Chelating Tricationic Porphyrin," *J. Am. Chem. Soc.,* 111:4998–5000, 1989.

Fiel, Robert J., "Porphyrin–Nucleic Acid Interactions: A Review," *Journal of Biomolecular Structure & Dynamics,* 6(6):1259–1275, 1989.

Vlassov et al., "Photoactivatable Porphyrin Oligonucleotide Derivatives for Sequence Specific Chemical Modification and Cleavage of DNA," *Nucleosides & Nucleotides,* 10(1–3):641–643, 1991.

Zuk et al., "Pharmacokinetic and Tissue Distribution Studies of the Photosensitizer bis(Di–Isobutyl Octadecysiloxy)Silicon 2,3–Naphthalocyanine (isoBosinc) in Normal and Tumor–Bearing Rats," *Photochemistry and Photobiology,* 59(1):66–72, 1994.

Lee et al., "Interaction of Psoralen–Derivatized Oligodeoxyribonucleoside Methylphosphonates with Single–Stranded DNA," *Biochemistry,* 27:3197–3203, 1988.

Bhan and Miller, "Photo–Cross Linking of Psoralen–Derivatized Oligonucleoside Methylphosphonates to Single–Stranded DNA," *Bioconjugate Chem.,* 1:82–88, 1990.

Boutorine et al., "Fullerene–Oligonucleotide Conjugates: Photo–Induced Sequence Specific DNA Cleavage", *Agnew. Chem. Int. Ed. Engl.,* 33(23/24):2462–2465, 1994.

Dolphin et al., "Porphocyanine: An Expanded Tetrapyrrolic Macrocycle," *J. Am. Chem. Soc.* 115:9301–9302, 1993.

Ehrenberg et al., "The Binding and Photosensitization Effects of Tetrabenzoporphyrins and Texaphyrin in bacterial Cells," *Lasers in Medical Science,* 8:197–203, 1993.

Le Doan et al., "Sequence–Targeted Photochemical Modifications of Nucleic Acids by Complementary Oligonucleotides Covalently Linked to Porphyrins," *Bioconjugate Chem.,* 1:108–113, 1990.

Le Doan et al., "Sequence–Specfic Recognition, Photocrosslinking and Cleavage of the DNA Double Helix by an Oligo–[α]–Thymidylate Covalently Attached to an Azidoproflavine," *Nucleic Acids Res.,* 15:7749–7760, 1987.

Levina et al., "Photomodification of RNA and DNA Fragments by Oligonucleotide Reagents Bearing Arylazide Groups," *Biochimie,* 75:25–27, 1993.

Mastruzzo et al., "Targeted Photochemical Modification of HIV–Derived Oligoribonucleotides by Antisense Oligodeoxynucleotides Linked to Porphyrins," *Photochem. Photobiol.,* 60(4):316–322, 1994.

Fedorova et al., "Palladium(II)–Coproporphyrin I as a Photoactivable Group in Sequence–Specific Modification of Nucleic Acids by Oligonucleotide Derivatives," *FEBS Lett.,* 259(2):335–337, 1990.

Morgan and Skalkos, "Second Generation Sensitizers: Where are We and Where Should We Be Going?" *Proc. SPIE Int. Soc. Opt. Eng. Ser.,* 6:87–106, 1990.

Perrouault et al., "Sequence–Specific Artificial Photo–Induced Endonucleases Based on Triple Helix–Forming Oligonucleotides," *Nature,* 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.,* 17(1):285–299, 1989.

Praseuth et al., "Sequence–Targeted Photosensitized Reactions in Nucleic Acids by Oligo–α–Deoxynucleotides and Oligo–β–Deoxynucleotides Covalently Linked to Proflavin," *Biochemistry,* 27:3031–3038, 1988.

Praseuth et al., "Sequence–Specific Binding and Photocrosslinking of α and β Oligodeoxynucleotides to the Major Groove of DNA via Triple–Helix Formation," *Proc. Natl. Acad. Sci. USA,* 85:1349–1353, 1988.

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA,* 88:5602–5606, 1991.

Teare and Wollenzien, "Specificity of Site Directed Psoralen Addition to RNA," *Nucleic Acids Res.,* 17(9):3359–3372, 1989.

Vogel et al., "New Porphycene Ligands: Octaethyl– and Etioporphycene (OEPc and EtioPc)–Tetra– and Pentacoordinated Zinc Complexes of OEPc," *Angew. Chem. Int. Ed. Engl.,* 32(11):1600–1604, 1993.

Wessel et al., "Porphyrins with Aromatic 26π–Electron Systems," *Agnew. Chem. Int. Ed. Eng.,* 32(8):1148–1151, 1993.

Agrawal et al., "Cellular Uptake and Anti–HIV Activity of Oligonucleotides and Their Analogs," *Gene Regulation: Biology of Antisense RNA and DNA,* 273–283 1992.

Agrawal and Tang, "Efficient Synthesis of Oligoribonucleotide and Its Phosphorothioate Analogue Using H–Phosphonate Approach," *Tetrahedron Letters,* 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA,* 133–145, 1992.

Basile et al., "Metal–Activated Hydrolytic Cleavage of DNA," *J. Am. Chem. Soc.,* 109:7550–7551, 1987.

Bradley et al., "Antisense Therapeutics," *Gene Regulation: Biology of Antisense RNA and DNA,* 285–293, 1992.

Breslow et al., "Effects of Metal Ions, Including $Mg^{2+}$ and Lanthanides, on the Cleavage of Ribonucleotides and RNA Model Compounds," *Proc. Natl. Acad. Sci. USA,* 88:4080–4083, 1991.

Browne and Bruice, "Chemistry of Phosphodiesters, DNA and Models. 2. The Hydrolysis of Bis(8–hydroxyquinoline) Phosphate in the Absense and Presence of Metal Ions," *Journal of the American Chemical Society,* 114(13):4951–4958, 1992.

Chin and Banaszczyk, "Rate–Determining Complexation in Catalytic Hydrolysis of Unactivated Esters in Neutral Water," *J. Am. Chem. Soc.,* 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.,* 111:4103–4105, 1989.

Chin et al., "Co(III) Complex Promoted Hydrolysis of Phosphate Diesters: Comparison in Reactivity of Rigid cis–Diaquotetraazacobalt(III) Complexes," *J. Am. Chem. Soc.,* 111:186–190, 1989.

Chin and Zou, "Catalytic Hydrolysis of cAMP," *Can. J. Chem.,* 65:1882–1884, 1987.

Chung et al., "Synthesis and Characterization of a Reactive Binuclear Co(III) Complex. Cooperative Promotion of Phosphodiester Hydrolysis," *Tetrahedron Letters,* 31(38):5413–5416, 1990.

Cohen, Jack S., "Chemically Modified Oligodeoxynucleotide Analogs as Regulators of Viral and Cellular Gene Expression," *Gene Regulation: Biology of Antisense RNA and DNA*, 247–259, 1992.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem. Soc.*, 114:9792–9795, 1992.

Komiyama et al., "Unprecedentedly Fast Hydrolysis of the RNA Dinucleoside Monophosphates ApA and UpU by Rare Earth Metal Ions," *J. Chem. Soc. Chem. Commun.*, 640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical Ribonucleases. 2. Synthesis and Characterization of Nucleoside–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.*, 114:1903–1905, 1992.

Ranganathan et al., "Design of a Chemical Nuclease Model with $(Lys)_2Cu$ as the Core Motif," *Journal of the Chemical Society*, 4:337–339, 1993.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remakably Fast Hydrolysis of 3',5'–Cyclic Adenosine Monophosphate by Cerium(III) Hydroxide Cluster," *J. Chem. Soc. Chem. Comm.*, 2 pages, 1992.

To and Neiman, "The Potential For Effective Antisense Inhibition of Retroviral Replication Mediated by Retroviral Vectors," *Gene Regulation: Biology of Antisense RNA and DNA*, 261–271, 1992.

Shelton and Morrow, "Catalytic Transesterification and Hydrolysis of RNA by Zinc(II) Complexes," *Inorg. Chem.*, 30:4295–4299, 1991.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolasa et al., "Trivalent Lanthanide Ions Do Not Cleave RNA in DNA–RNA Hybrids", *Inorg. Chem.*, 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.*, 32(12):1716–1719, 1993.

Hayashi et al., "Site-Selective Hydrolysis of tRNA by Lanthanide Metal Complexes," *Inorg. Chem.*, 32:5899–5900, 1993.

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic, Anionic, and Neutral Substrates, in Transition Metals in Supramolecular Chemistry," L. Fabbrizzi and A. Poggi, Editors, NATO ASI Series, Kluwer, Amsterdam, pp. 391–408, 1994.

CHROMOPHORE PROBE FOR DETECTION OF NUCLEIC ACID

This application is a continuation-in-part application of U.S. Ser. No. 08/310,501, allowed filed Sep. 21, 1994, which is a continuation-in-part application of U.S. Ser. No. 08/112, 872 filed Aug. 25, 1993, now U.S. Pat. No. 5,451,576, and of International application No. PCT/US94/06284 designating the United States and filed Jun. 9, 1994. U.S. Ser. No. 08/112,872 is a divisional application of U.S. Ser. No. 07/822,964 filed Jan. 21, 1992, now U.S. Pat. No. 5,252,720. PCT/US94/06284 is a continuation-in-part application of U.S. Ser. No. 08/227,370 allowed filed Apr. 14, 1994, which is a continuation-in-part application of U.S. Ser. No. 08/075, 123 filed Jun. 9, 1993, now abandoned, which is a continuation-in-part of U.S. Ser. No. 07/822,964 filed Jan. 21, 1992, now U.S. Pat. No. 5,252,720. All of the above-named patents are incorporated by reference herein.

FIELD OF THE INVENTION

The present invention relates to a method of detecting nucleic acid targets, and particularly to chromophore probes for use in such detection.

BACKGROUND OF THE INVENTION

The texaphyrins are certain "expanded porphyrins" which have been found to be useful as MRI contrast agents, as radiation sensitizers and in photodynamic therapy (PDT), as well as having the ability to hydrolytically cleave phosphate esters, including RNA, and to photolyrically cleave RNA and DNA. Texaphyrin is considered as being an aromatic benzannulene containing both 18π- and 22π-electron delocalization pathways. See, e.g., Sessler, J. L. et al., *Accounts of Chemical Research*, 1994, 27, 43. Texaphyrins and water-soluble texaphyrins and method of preparation have been described in U.S. Pat. Nos. 4,935,498; 5,252,720; 5,256, 399; 5,272,142; and 5,292,414; and in International publn.s WO 94/29316 and WO 95/01996; all of which are incorporated herein by reference.

SUMMARY OF THE INVENTION

The present invention is directed to chromophoric probes for use in detecting nucleic acid sequences. More particularly, the invention is directed to probes that comprise a texaphyrin chromophore molecule covalently coupled or conjugated to a site-directing molecule, the site-directing molecule having affinity for a biological receptor or a nucleic acid sequence.

In one embodiment of the invention, the probe comprises a texaphyrin chromophore conjugated to an oligonucleotide having complementary binding affinity for a target nucleic acid sequence.

In another embodiment of the invention, the probe comprises an oligonucleotide conjugated with a texaphyrin chromophore on either the 5'- or the 3'-end and having an amine on the other end. The oligonucleotide has binding complementarity with the nucleic acid sequence of the target nucleic acid and comprising a partial inverted repeat nucleic acid sequence.

In yet another embodiment, the invention is directed to a probe comprising an oligonucleotide conjugated with a first texaphyrin, which exhibits fluorescence, on either the 5'- or the 3'-end and also conjugated to a second texaphyrin, which has lower excited state energetics as compared to the first

2 texaphyrin, on the other end. The oligonucleotide has a nucleic acid sequence that is complementary to the nucleic acid sequence of the target nucleic acid and comprising a partial inverted repeat nucleic acid sequence.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Fluorescent molecules contain chromophores that can be photochemically promoted to an excited state, or higher energy level, by irradiating them with light. Excitation wavelengths are generally in the UV, blue, or green regions of the spectrum. Chromophores can remain in the excited state for about $10^{-9}$ seconds before releasing their energy and returning to the ground state. Those chromophores that dissipate their energy as emitted light are fluorescent. The wavelength distribution of the outgoing photons forms the emission spectrum, which peaks at longer wavelengths (lower energies) than the excitation spectrum, but is equally characteristic for a particular fluorophore.

Texaphyrins are unique as chromophores in that they both absorb and emit light in the red light region, about 700–800 nm wavelengths. The fluorescence emission for texaphyrins occurs about 5–40 nm farther to the red wavelengths in relation to the absorbing wavelengths. Thus, texaphyrins have particular utility in biolocalization and clinical diagnostics and also in in vitro applications such as laboratory and medical research, industry, and agriculture.

Optical characteristics of certain texaphyrin complexes are described in Sessler et al. (1991), incorporated herein by reference. The absorption and emission wavelengths and the amount of fluorescence exhibited by the texaphyrins will vary, depending on the substituents attached to the texaphyrin molecule, the metal with which the texaphyrin forms a complex, and other factors. It has been found that the presence of a metal will often decrease the fluorescence of texaphyrins and that certain Cd-texaphyrin complexes have a comparatively weak fluorescence (Sessler, et al., 1991). The Lu-T2BET complex (cpd. $1_B$, M=Lu) has a very strong fluorescence with a maximum at 747 nm and a lifetime of (380±15)ps (measured by time-correlated, single-photon counting), whereas the Gd-T2B2 complex (cpd. $1_A$, M=Gd) has very weak fluorescence.

1<sub>A</sub> R<sub>7</sub>=R<sub>8</sub>=OCH<sub>2</sub>CH<sub>2</sub>CH<sub>2</sub>OH

1<sub>B</sub> R<sub>7</sub>=R<sub>8</sub>=O(CH<sub>2</sub>CH<sub>2</sub>O)<sub>3</sub>CH<sub>2</sub>CH<sub>2</sub>OCH<sub>3</sub>

A particular use of the present invention is the detection and diagnosis of certain types of tissue such as tumors and tumor cells and atheromatous tissue. Texaphyrin compounds show a high intrinsic biolocalization selectivity for lipid-rich tissues such as tumors or neoplastic tissues and atheromas. A texaphyrin complex which exhibits fluorescence is administered to a host, after which the host is exposed to activating light in the 700–800 nm range and the location of the tumor or atheroma is observed as a result of fluorescent light emitted by the localized texaphyrin. A particular advantage to this technology is in cardiovascular applications where atheromatous plaque is "seen" and "obliterated" using only one agent for both detection and treatment. An automated feedback loop is envisioned where the light dose is controlled by the amount of fluorescence emitted. Therefore, light would be provided only to those sites where high initial fluorescence is seen. Such an automated irradiation system has the advantage of using only a single catheter in a clinical setting.

Another embodiment of the use of the present invention is in the detection and subsequent destruction of tumor or atheromatous tissue. A texaphyrin-diamagnetic metal complex which exhibits fluorescence and also exhibits biolocalization in atheromatous and tumor tissue relative to surrounding tissue is administered to a host. Localization sites of the complex in the host are determined by fluorescence of the complex. The complex is then photoirradiated in proximity to the localization sites, such as with the use of a laser or fiber optics, to cause tumor or atheroma tissue destruction by photodynamic therapy.

In another use of the present invention, a texaphyrin molecule, either alone or conjugated to a site-directing molecule, provides a probe, reagent, or assay for detection of a particular target by fluorescence scanning technology. In some instances, such as with certain viruses, the texaphyrin itself attaches to the target without the need for an additional site-directing molecule.

Representatives of texaphyrins which may be activated and attached to nucleotides following the present invention are included within the following structure I:

In this texaphyrin, M is H or a divalent or a trivalent metal; $R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyatkyl, saccharide, carboxy, carboxyalkyl, carboxyamide, carboxyamidealkyl, aminoalkyl, sulfonatoalkyl, amidealkyl, aryl, or a couple to a site-directed molecule; $R_6$ and $R_9$ are independently selected from the groups of $R_1$–$R_4$, $R_7$ and $R_8$, with the proviso that the halide is other than iodide and the haloalkyl is other than iodoalkyl; $R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple to a saccharide or to a site-directed molecule; and Z will typically be less than or equal to 5.

In the probes of the present invention, at least one of $R_1$–$R_{12}$ will be covalently coupled to a site-directed molecule. In a preferred embodiment of the invention, the site-directed molecule is an oligonucleotide, and the oligonucleotide has complementarity with, or binding affinity for, a nucleic acid sequence that is to be targeted by the probe.

In the context of the basic macrocycle with a divalent or trivalent metal cation, Z is 1 or 2; however, one skilled in the art in light of the present disclosure would realize that the complexes described in the present invention may have one or more additional ligands providing charge neutralization and/or coordinative saturation to the metal ion. Such ligands include chloride, nitrate, acetate, and hydroxide, among others. The value of Z would also be altered due to charges present on, for example, a covalently attached site-directed molecule, such as negative charges of the phosphate groups on an oligonucleotide.

Where the texaphyrin is a chromophore or exhibits fluorescence, M is H or is a diamagnetic metal cation, and is preferably Lu(III). Where the texaphyrin is the second texaphyrin in a probe having two texaphyrin molecules according to this invention, M is a paramagnetic metal cation or is a diamagnetic metal cation having lower excited state energetics as compared to the first texaphyrin molecule.

"Alkyl" means alkyl groups, straight, branched or as cyclic isomers, with generally one to fifty, preferably one to thirty, more preferably one to ten, carbon atoms.

"Alkenyl" means alkenyl groups, straight, branched or as cyclic isomers, with generally two to fifty, preferably two to thirty, more preferably two to ten, carbon atoms, and with one to five or more double bonds, preferably one to five, more preferably one to three double bonds.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$alkyls being preferred, and diols of $C_{1-3}$alkyls being more preferred; and polyethylene glycol, polypropylene glycol and polybutylene glycol as well as polyalkylene glycols containing combinations of ethylene, propylene and butylene.

"Oxyalkyl" means alkyl groups as herein described with oxygen atoms, including ether or ester linkages. The number of repeating oxyalkyls within a substituent may be up to 200, preferably from 1 to 20, more preferably from 1 to 7, and most preferably is 2–3.

"Hydroxyalkoxy" means alkyl groups as described herein having ether or ester linkages, as well as hydroxyl groups, substituted hydroxyl groups, carboxyl groups, substituted carboxyl groups or the like.

"Carboxy" groups include carboxylic acids of the alkyls described herein as well as aryl carboxylic acids such as benzoic acid. "Carboxyalkyl" means alkyl groups having hydroxyl groups, carboxyl or amide substituted ethers, ester linkages, tertiary amide linkages removed from the ether or the like. Representative examples of "carboxyamides" include primary carboxyamides ($CONH_2$), and secondary (CONHR') and tertiary (CONR'R") carboxyamides where each of R' and R" is a functional group as described herein. "Carboxyamidealkyl" means alkyl groups with hydroxyl groups, secondary or tertiary amide linkages or the like.

Representatives of useful amines include a primary, secondary or tertiary amine of an alkyl as described hereinabove.

"Aryl" may be a phenyl group, unsubstituted or substituted with a nitro, carboxy, sulfonic acid, hydroxy, oxyalkyl, or halide.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as open chain forms of various sugars, and the like. Examples of amine-derivatized sugars are galactosamine, glucosamine, and sialic acid.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether, or the like.

For the above-described texaphyrins, hydroxyalkoxy may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to $((2n+1)-2x)$. The hydroxyalkoxy or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10,y is zero or a positive integer less than $((2n+1)-q)$, q is zero or a positive integer less than or equal to 2n+1, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or a site-directed molecule or catalytic group. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to 2m+1, and $R^b$ is independently H, alkyl, hydroxyalkyl, or saccharide. In a preferred embodiment, $R^a$ is an oligonucleotide.

Carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than $((2n+1)-q)$, q is zero or a positive integer less than or equal to 2n+1, and $R^c$ is $(CH_2)_nCO_2R^d$, $(CH_2)_nCONHR^d$, $(CH_2)_nCON(R^d)_2$ or a site-directed molecule or catalytic group. In this case, n is a positive integer from 1 to 10, $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to 2m+1, and $R^b$ is independently H, alkyl, hydroxyalkyl, or saccharide. In a preferred embodiment, $R^c$ is an oligonucleotide.

Exemplary site-directed molecules useful herein include, but are not limited to, polydeoxyribonucleotides; oligodeoxyribonucleotides; polyribonucleotide analogs; oligoribonucleotide analogs; polyamides; molecules having affinity for a biological receptor, such as peptides, enzyme inhibitors, and proteins such as antibodies; steroids and steroid derivatives; hormones such as estradiol or histamine, and hormone mimics such as morphine; and further macrocycles such as sapphyrins and rubyrins.

The oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. The alkenyl group is preferably allyl. The alkyl group is preferably a methyl group and the methyl group is attached to the 2' oxygen of the ribose. Other alkyl groups may be ethyl or propyl.

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates and phosphoramidates and the like. Deoxyribonucleotides, deoxyribonucleotide analogs and ribonucleotide analogs are contemplated as site-directed molecules in the present invention.

The term "texaphyrin-oligonucleotide conjugate" means that an oligonucleotide is attached to the texaphyrin in a 5' or a 3' linkage. The oligonucleotide or other site-directed molecule may be attached either directly to the texaphyrin or to the texaphyrin via a linker or a couple of variable length.

A conjugate group having site specificity may be covalently coupled to a texaphyrin directly on the macrocycle ring or through various couples. A couple may be described as a linker, i.e., the covalent product formed by reaction of a reactive group designed to attach covalently another molecule at a distance from the texaphyrin macrocycle. Exemplary linkers or couples are amides, amine, thiol, thioether, ether, or phosphate covalent bonds as described in the examples for attachment of oligonucleotides. In preferred embodiments, conjugates and appended groups are covalently bonded to the texaphyrin via a carbon-carbon, a carbon-nitrogen, a carbon-sulfur, or a carbon-oxygen bond, more preferred being a carbon-oxygen or a carbon-nitrogen bond.

In presently preferred texaphyrins, $R_1$ is hydroxyalkyl and $R_2$, $R_3$ and $R_4$ are alkyl. Alternatively, $R_3$ may be a couple to a site-directed molecule, preferably a couple to an oligonucleotide. In a further presently preferred texaphyrin, $R_1$ is $CH_2CH_3$ or $(CH_2)_2CH_2OH$, $R_2$ and $R_3$ are $CH_2CH_3$, $R_4$ is $CH_3$, and $R_7$ and $R_8$ are $OCH_2CH_2CH_2OH$ or $R_7$ and $R_8$ are $O(CH_2CH_2O)_tCH_2CH_2OR'$ where t is 0–200, preferably 2–100, and R' is H or $CH_3$. Alternatively, $R_7$ is a couple to a site-directed molecule, preferably a couple to an oligonucleotide, more preferably $O(CH_2)_nCO$—where n is 1–7 and preferably 1–3; and $R_8$ is H, $CH_3$ or $OCH_3$. In a further presently preferred embodiment, $R_1$ is $CH_2CH_3$ or $(CH_2)_2CH_2OH$, $R_2$ and $R_3$ are $CH_2CH_3$, $R_4$ is $CH_3$, $R_7$ is $O(CH_2CH_2O)_tCH_2CH_2OR'$ where t is 0–200, preferably 2–100, and R' is H or $CH_3$, and $R_8$ is a couple to a site-directed molecule, preferably a couple to an oligonucleotide, more preferably $O(CH_2)_nCO$— where n is 1–7 and preferably 1–3.

Texaphyrin compounds, texaphyrin-site directed molecule conjugates and texaphyrin-oligonucleotide conjugates and methods of making are described in the patents and applications previously referenced herein.

EXAMPLE 1

Fluorescence Detection of Texaphyrins

Figure 1:
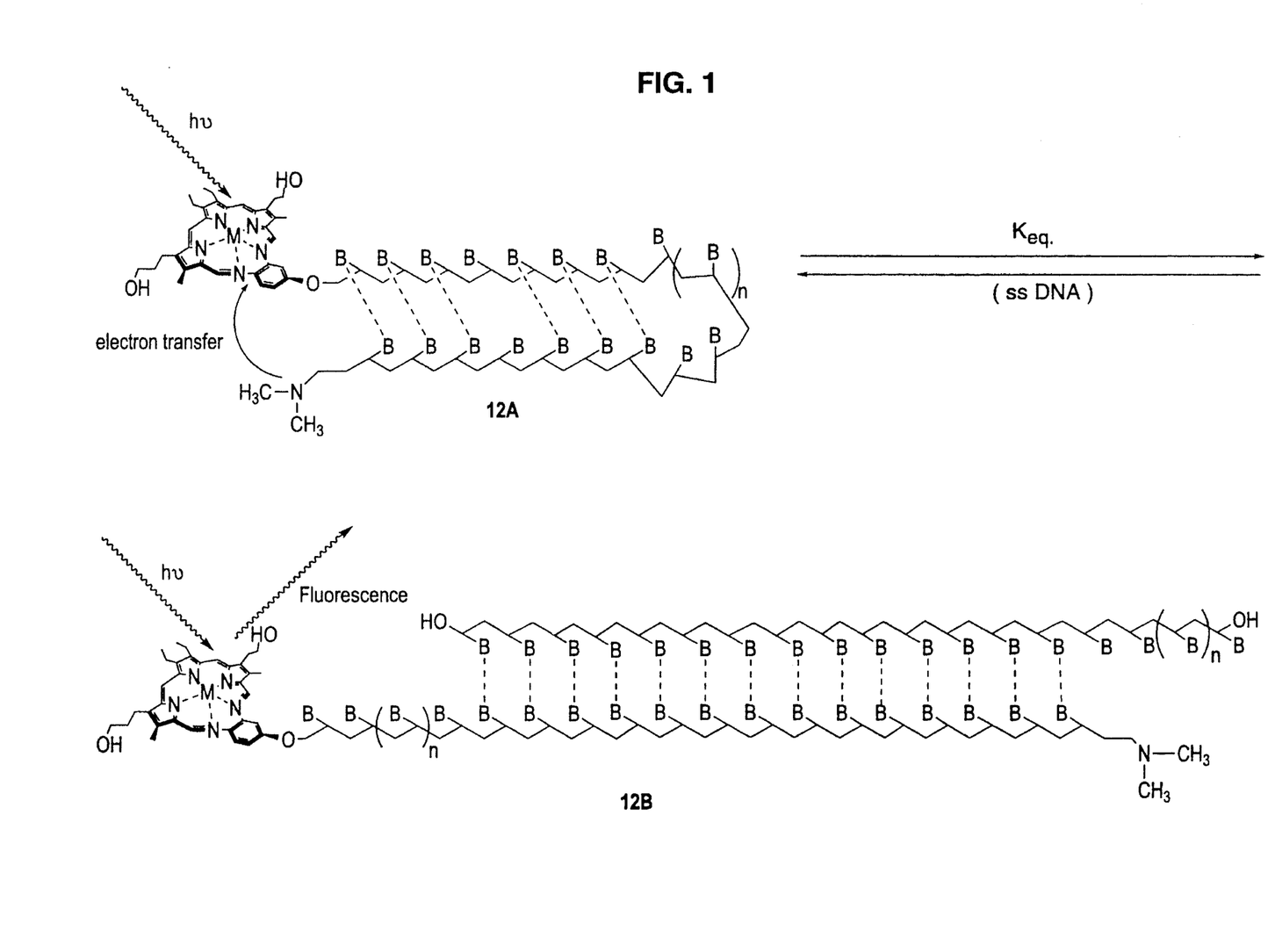
FIG. 1 depicts a texaphyrin "fluorescent switch" for detecting a sequence in DNA as described in Example 1. "B" represents a base present in nucleic acid.

Using stepwise DNA synthesis, methods of which are disclosed in U.S. Ser. No. 08/310,501, the disclosure of which is incorporated herein by reference, a DNA probe may be prepared which bears a texaphyrin chromophore on either the 5'- or the 3'-end and an amine on the other end. The sequence is designed as a partial inverted repeat sequence such that the DNA probe forms a relatively weak intramolecular complex called a hairpin, which brings the texaphyrin and amine groups into close proximity ($12_A$ of FIG. 1). As a consequence of this proximity, the excited electronic state produced by irradiation of the texaphyrin chromophore is rapidly quenched by an electron from the amine group, and is not able to fluoresce or phosphoresce. When a second nucleic acid is present, however, which is complementary in sequence to the probe, a duplex forms that is stronger in its absolutely binding affinity than the intrastrand hairpin which, in effect, separates the texaphyrin chromophore from the amine ($12_B$ of FIG. 1). The excited electronic state produced by irradiation of the texaphyrin chromophore is no longer quenched by the amine group and is able to fluoresce. The probe as described thus acts as a "molecular switch", such that an observable signal is returned upon irradiation only in the presence of the complementary nucleic acid. In some applications, mismatches would be allowed in the inverted repeat since it is known that nucleic acids having mismatches will hybridize to each other, albeit less strongly than a perfect match.

Figure 2:
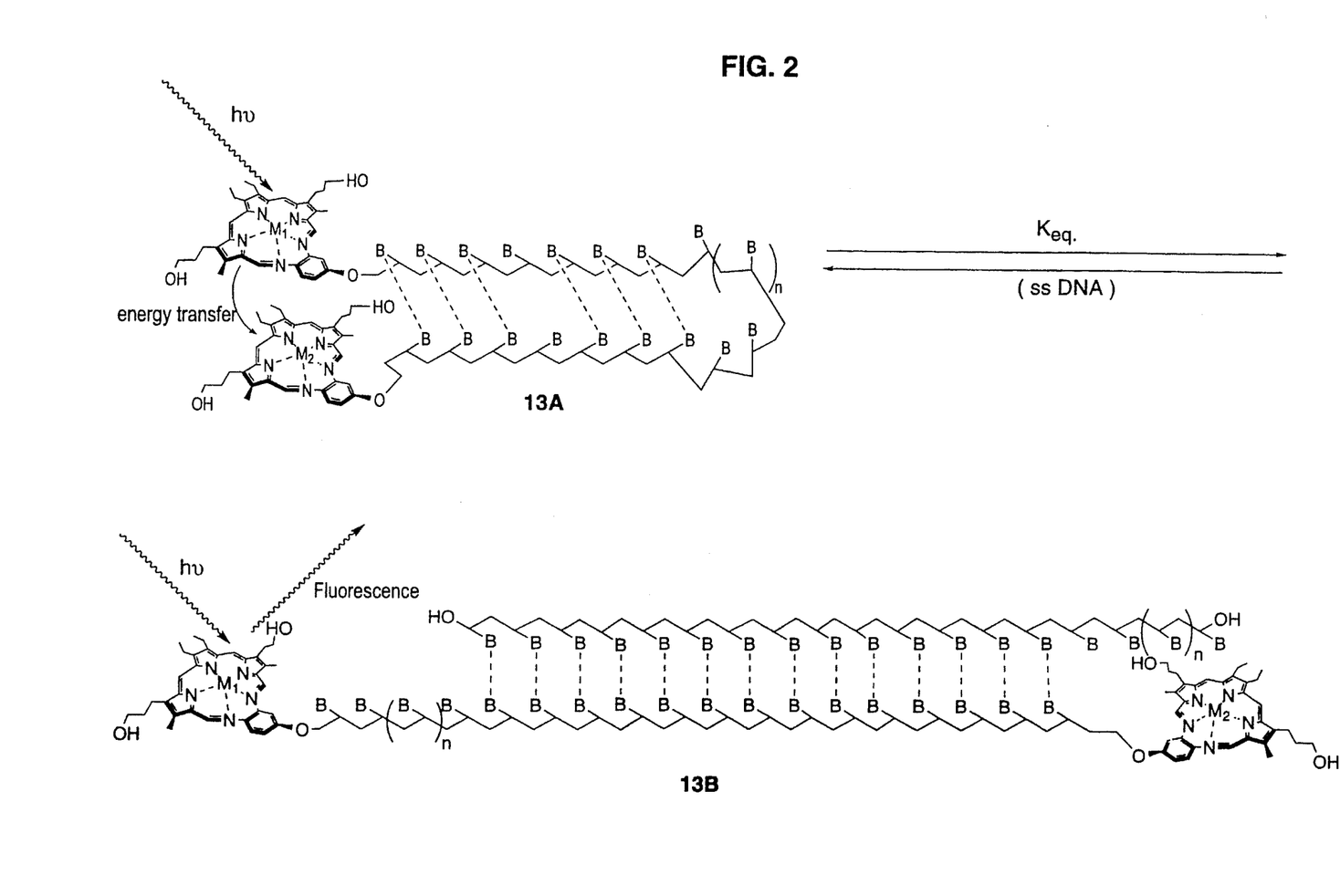
FIG. 2 depicts a further texaphyrin "fluorescent switch" for detecting a sequence in DNA having a different texaphyrin at each end of the probe as described in Example 1. $M_1$ is H or a diamagnetic metal cation, $M_2$ is a paramagnetic metal cation or a diamagnetic metal cation with lower excited state energetics as compared to $M_1$. "B" represents a base present in nucleic acid.

A modification of this concept is illustrated in FIG. 2. Here, two different texaphyrin chromophores are used. The first of these (the one with $M_1$) is fluorescent by virtue of either containing a diamagnetic metal such as Lu(III) or La(III) or no metal at all (M=H). The second texaphyrin (the one with $M_2$) contains a paramagnetic metal center such as, e.g., Gd(III), Eu(III), etc. It thus replaces the tertiary amine of FIG. 1, but would quench the fluorescence in the hairpin "state" as the result of energy or exciton transfer from the diamagnetic ($M_1$) texaphyrin excited state produced by irradiation to the paramagnetic ($M_2$) texaphyrin. In the duplex form ($13_B$), such energy transfer fluorescence quenching would be precluded as a result of the larger spatial separation between the diamagnetic $M_1$ texaphyrin donor and the paramagnetic $M_2$ texaphyrin acceptor. Thus, the "switch" is "turned on" due to the greater fluorescence lifetime of the $M_1$ texaphyrin and is further able to perform repeatedly.

Such a probe might find application in developing an in vitro assay for the presence of a particular nucleic acid sequence. For example, a probe might be designed which fluoresces only upon hybridizing with an invariant sequence from the HIV genome, and thus may serve as an efficient way of screening for this virus in blood. Other chromophores such as porphyrins and other fluorescent dyes may serve the purpose, but the texaphyrin has the advantage of a red shifted absorbance. Other groups besides an amine may serve as the electron donor, eg., a carotenoid. A key feature of the system as described is that a positive signal (eg., fluorescence) is given in the presence of the analyte. It is important to note that the intermolecular duplex is able to compete with the intramolecular hairpin due to the extra stability obtained by binding to the bases in the loop region. Also, as an intramolecular complex (the hairpin) is by definition concentration-independent, the assay can be carried out at a sufficiently low concentration of probe such that intermolecular quenching by another probe does not occur. Thus the equilibrium between open (fluorescent) and closed forms of the probe depends solely on the concentration of the analyte.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods, and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A probe for the detection of a target nucleic acid sequence, which probe comprises a texaphyrin chromophore conjugated to an oligonucleotide having complementary binding affinity for said targeted nucleic acid sequence.

2. A probe for the detection of a target nucleic acid sequence, which probe comprises an oligonucleotide comprising a texaphyrin chromophore on either the 5'- or the 3'-end and an amine on the other end, said oligonucleotide having complementary binding affinity for said target nucleic acid and comprising a partial inverted repeat nucleic acid sequence.

3. A probe for the detection of a target nucleic acid sequence, which probe comprises an oligonucleotide conjugated to a first texaphyrin, which exhibits fluorescence, on either the 5'- or the 3'-end and also conjugated to a second texaphyrin, which has lower excited state energetics as compared to the first texaphyrin, on the other end; said oligonucleotide having complementary binding affinity for said target nucleic acid and comprising a partial inverted repeat nucleic acid sequence.

4. The probe of claim 1 wherein the texaphyrin chromophore has the structure wherein M is H, a divalent metal cation, or a trivalent metal cation;

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, or a couple that is coupled to the oligonucleotide;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple that is coupled to a saccharide or to the oligonucleotide; and

Z is an integer value less than or equal to 5.

5. The probe of claim 4 wherein M is a trivalent metal cation, and the trivalent metal cation is Lu(III), Y(III), or La(III).

6. The probe of claim 4 wherein $R_1$ is $CH_2CH_3$ or $(CH_2)_2CH_2OH$; $R_2$ and $R_3$ are $CH_2CH_3$; $R_4$ is $CH_3$; $R_7$ is a couple that is coupled to the oligonucleotide; and $R_8$ is H, $CH_3$, or $OCH_3$.

7. The probe of claim 4 wherein $R_1$ is $CH_2CH_3$ or $(CH_2)_2CH_2OH$; $R_2$ and $R_3$ are $CH_2CH_3$; $R_4$ is $CH_3$; $R_7$ is $O(CH_2CH_2O)_tCH_2CH_2OR'$ where t is 2–100, and R' is H or $CH_3$; and $R_8$ is a couple that is coupled to an oligonucleotide.

8. The probe of claim 2 wherein the texaphyrin chromophore has the structure wherein M is H, a divalent metal cation, or a trivalent metal cation;

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, or a couple that is coupled to the oligonucleotide;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple that is coupled to a saccharide or to the oligonucleotide; and Z is an integer value less than or equal to 5.

9. The probe of claim 8 wherein M is a trivalent metal cation, and the trivalent metal cation is Lu(III), Y(III), or La(III).

10. The probe of claim 2 wherein the partial inverted repeat nucleic acid sequence forms an intramolecular hairpin complex thereby positioning the texaphyrin and the amine into close proximity and causing quenching of fluorescence of the texaphyrin upon irradiation.

11. The probe of claim 10 further comprising the target nucleic acid wherein a duplex is formed between the probe and the target nucleic acid thereby separating the texaphyrin chromophore from the amine and allowing the texaphyrin chromophore to fluoresce upon irradiation.

12. The probe of claim 11 wherein the target nucleic acid is an invariant sequence from an HIV genome, the probe thereby serving as a means for screening for presence of HIV virus.

13. The probe of claim 3 wherein the first texaphyrin has the structure wherein

M is H, a divalent metal cation, or a trivalent metal cation;

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, or a couple that is coupled to the oligonucleotide;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple that is coupled to a saccharide or to the oligonucleotide; and Z is an integer value less than or equal to 5.

14. The probe of claim 13 wherein M is a trivalent metal cation, and the trivalent metal cation is Lu(III), Y(III), or La(III).

15. The probe of claim 3 wherein the partial inverted repeat nucleic acid sequence forms an intramolecular hairpin complex thereby positioning the first texaphyrin and the second texaphyrin into close proximity and causing quenching of fluorescence of the first texaphyrin upon irradiation.

16. The probe of claim 15 further comprising the target nucleic add wherein a duplex is formed between the probe and the target nucleic acid thereby separating the first texaphyrin from the second texaphyrin and allowing the first texaphyrin to fluoresce upon irradiation.

17. The probe of claim 16 wherein the target nucleic acid is an invariant sequence from an HIV genome, the probe thereby serving as a means for screening for presence of HIV virus.

18. The probe of claim 3 wherein the second texaphyrin has the structure wherein M is a paramagnetic metal cation or a diamagnetic metal cation having lower excited state energetics as compared to the first texaphyrin;

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, or a couple that is coupled to the oligonucleotide;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple that is coupled to a saccharide or to the oligonucleotide; and Z is an integer value less than or equal to 5.

19. The probe of claim 18 wherein M is a paramagnetic metal cation, and the paramagnetic metal cation is Gd(III) or Eu(III).

20. The probe of claim 3 wherein the first texaphyrin is complexed with Lu(III) or Y(III), and the second texaphyrin is complexed with Gd(III).

* * * * *

UNITED STATES PATENT AND TRADEMARK OFFICE
CERTIFICATE OF CORRECTION

PATENT NO. : 5,595,726
DATED : January 21, 1997
INVENTOR(S) : Darren Magda et al.

It is certified that error appears in the above-identified patent and that said Letters Patent is hereby corrected as shown below:

At column 8, line 17, immediately following "Lu(III)" insert --, Y(III),--.

Signed and Sealed this

First Day of September, 1998

Attest:

BRUCE LEHMAN

Attesting Officer

Commissioner of Patents and Trademarks